(12) United States Patent
Roifman et al.

(10) Patent No.: US 7,563,820 B2
(45) Date of Patent: Jul. 21, 2009

(54) COMPOUNDS FOR MODULATING CELL PROLIFERATION

(75) Inventors: Chaim M. Roifman, North York (CA); Peter Demin, Moscow (RU); Thomas Grunberger, Toronto (CA); Olga Rounova, Moscow (RU); Octavian Laurand Cimpean, Thornhill (CA)

(73) Assignee: The Hospital for Sick Children, Toronto, Ontario (CA)

( * ) Notice: Subject to any disclaimer, the term of this patent is extended or adjusted under 35 U.S.C. 154(b) by 419 days.

(21) Appl. No.: 10/501,699

(22) PCT Filed: Jan. 17, 2003

(86) PCT No.: PCT/CA03/00032

§ 371 (c)(1), (2), (4) Date: Jul. 16, 2004

(87) PCT Pub. No.: WO03/062190

PCT Pub. Date: Jul. 31, 2003

(65) Prior Publication Data

US 2005/0085538 A1 Apr. 21, 2005

Related U.S. Application Data

(60) Provisional application No. 60/349,214, filed on Jan. 18, 2002, provisional application No. 60/349,215, filed on Jan. 18, 2002, provisional application No. 60/349,216, filed on Jan. 18, 2002.

(51) Int. Cl.
C07C 255/03 (2006.01)
A61K 31/275 (2006.01)

(52) U.S. Cl. ..................................... 514/521
(58) Field of Classification Search ............... 514/521; 558/398
See application file for complete search history.

(56) References Cited

U.S. PATENT DOCUMENTS 3,718,472 A 2/1973 Oliver et al.
4,617,373 A 10/1986 Pruett
4,632,895 A 12/1986 Patel
5,789,427 A 8/1998 Chen

FOREIGN PATENT DOCUMENTS

| CA | 1264594 | 1/1990 |
|---|---|---|
| JP | 2001066605 | 3/2001 |
| WO | WO-95/24190 | 9/1995 |
| WO | WO-96/40629 | 12/1996 |
| WO | WO-01/79158 | 10/2001 |
| WO | WO-03/062190 | 7/2003 |

OTHER PUBLICATIONS

Zhong et al., "Catalytic synthesis of alpha-cyano, beta-unsaturated sulfones in the presence of organotellurium oxide," Chinese Chemical Letters 2(9):683-684 (1991).
Schroder et al., "Arzneimittelchemi passage," Arzeimittelchemi Grundlagen Nerven Muskeln und Gewebe pp. 30-33 (1976).

*Primary Examiner*—James O Wilson
*Assistant Examiner*—Ebenezer Sackey
(74) *Attorney, Agent, or Firm*—Omar A. Nassif

(57) ABSTRACT

The following compounds of formulae (I) and (III) which may be useful in treating a variety of cell proliferative disorders are disclosed: Formula (I), (II), wherein $R^1$, $R^2$ and $R^3$ are each independently selected from H, OH, $C_{1-6}$alkyl, $C_{1-6}$alkoxy, $NH_2$, NH—$C_{1-6}$alkyl, N($C_{1-6}$alkyl), SH, S—$C_{1-6}$alkyl, $NO_2$, $CF_3$, $OCF_3$ and halo; $R^4$ is unsubstituted Ar, or Ar substituted with 1-4 substituents, independently selected from $C_{1-6}$alkyl, $C_{1-6}$alkoxy and halo; X is selected from $(CH_2CH_2O)_n$ and $(CH_2)_n$, and n=1-4.

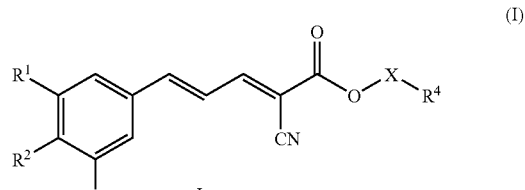

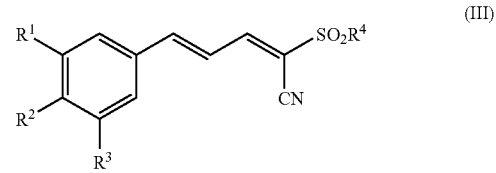

15 Claims, No Drawings

COMPOUNDS FOR MODULATING CELL PROLIFERATION

RELATED APPLICATIONS

This application is a national stage filing under 35 U.S.C. 371 of International Application PCT/CA03/00032, filed Jan. 17. 2003, which claims priority from U.S. Provisional Applications Ser. Nos. 60/349,214, 60/349,215, and 60/349,216, each filed on Jan. 18, 2002, the specifications of each of which are incorporated by reference herein. International Application PCT/CA03/00032 was published under PCT Article 21(2) in English.

FIELD OF THE INVENTION

This invention relates to compounds and their use for treating a variety of cell proliferative disorders.

BACKGROUND OF THE INVENTION

A number of small molecules which act as tyrosine kinase inhibitors have been identified. For example, certain compounds have been described as tyrosine kinase inhibitors, effective to inhibit cell proliferation (see for example, U.S. Pat. Nos. 5,891,917, 5,217,999, 5,773,476, 5,935,993, 5,656,655, 5,677,329, 5,789,427 and WO 01/79158). However, there remains a need for compounds that selectively target one or more such kinases, e.g., to preferentially inhibit proliferation of cancerous cells over normal cell proliferation.

SUMMARY OF THE INVENTION

Compounds are provided that may be used for modulating abnormal cell proliferation, for example inhibiting cancer cell proliferation, and which preferably do not adversely affect normal cell proliferation.

Accordingly, the present invention includes compounds of Formula I and salts, solvates and hydrates thereof:

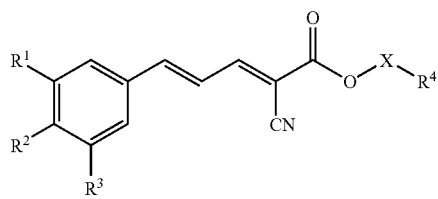

wherein
$R^1$, $R^2$, $R^3$ are each independently selected from H, OH, $C_{1-6}$alkyl, $C_{1-6}$alkoxy, $NH_2$, $NH$—$C_{1-6}$alkyl, $N(C_{1-6}$alkyl)($C_{1-6}$alkyl), SH, S—$C_{1-6}$alkyl, $NO_2$, $CF_3$, $OCF_3$ and halo;
$R^4$ is unsubstituted Ar, or Ar substituted with 1-4 substituents, independently selected from $C_{1-6}$alkyl, $C_{1-6}$alkoxy and halo;
X is selected from $(CH_2CH_2O)_n$ and $(CH_2)_n$, and n=1-4.

In certain embodiments, X is $(CH_2)_n$.

The present invention also provides compounds of Formula II and salts, solvates and hydrates thereof:

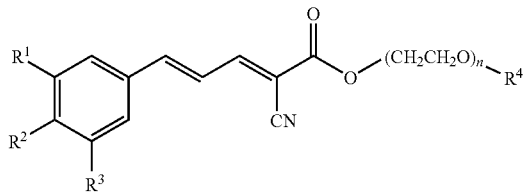

wherein
$R^1$, $R^2$, $R^3$ are each independently selected from H, OH, $C_{1-6}$alkyl, $C_{1-6}$alkoxy, $NH_2$, $NH$—$C_{1-6}$alkyl, $N(C_{1-6}$alkyl)($C_{1-6}$alkyl), SH, S—$C_{1-6}$alkyl, $NO_2$, $CF_3$, $OCF_3$ and halo;
$R^4$=$C_{1-6}$alkyl; and
n=1-4.

Additionally, the present invention includes compounds of Formula III and salts, solvates and hydrates thereof:

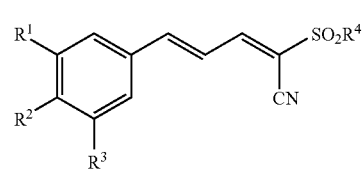

wherein
$R^1$, $R^2$ and $R^3$ are each independently selected from H, OH, $C_{1-6}$alkyl, $C_{1-6}$alkoxy, $NH_2$, $NH$—$C_{1-6}$alkyl, $N(C_{1-6}$alkyl)($C_{1-6}$alkyl), SH, S—$C_{1-6}$alkyl, $NO_2$, $CF_3$, $OCF_3$ and halo; and
$R^4$ is selected from $C_{1-6}$alkyl, phenyl and pyridyl, wherein phenyl and pyridyl are unsubstituted or substituted with 1-4 substituents, independently selected from $C_{1-6}$alkyl, $C_{1-6}$alkoxy and halo, with the provisos that when $R^1$ and $R^3$ are both H and $R^4$ is unsubstituted phenyl, $R^2$ is not H, Cl, or $OCH_3$; when $R^1$ and $R^2$ are both H and $R^4$ is unsubstituted phenyl, $R^3$ is not $NO_2$; and when $R^1$ and $R^3$ are both H and $R^4$ is $CH_3$, $R^2$ is not $N(CH_3)_2$.

In accordance with a further aspect of the present invention, there are provided compounds of Formula IV and salts, solvates and hydrates thereof, for use in compositions and methods for treating cell proliferation:

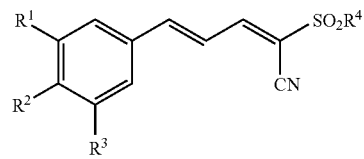

wherein
$R^1$, $R^2$ and $R^3$ are each independently selected from H, OH, $C_{1-6}$alkyl, $C_{1-6}$alkoxy, $NH_2$, $NH$—$C_{1-6}$alkyl, $N(C_{1-6}$alkyl)($C_{1-6}$alkyl), SH, S—$C_{1-6}$alkyl, $NO_2$, $CF_3$, $OCF_3$ and halo; and
$R^4$ is selected from $C_{1-6}$alkyl, phenyl and pyridyl, wherein phenyl and pyridyl are unsubstituted or substituted with 1-4 substituents, independently selected from $C_{1-6}$alkyl, $C_{1-6}$alkoxy and halo.

According to another aspect of the present invention, there is provided a pharmaceutical composition comprising a compound as set forth herein and a pharmaceutically acceptable carrier or diluent.

In accordance with a further aspect of the present invention, there is provided a method for modulating cell proliferation, preferably inhibiting cell proliferation, comprising administering an effective amount of a compound as set forth herein to a cell or animal in need thereof. The invention also includes a use of a compound as set forth herein to modulate cell proliferation, preferably inhibit cell proliferation, for example in cancer cells. The invention further provides for a use of a compound as set forth herein to prepare a medicament to modulate cell proliferation, preferably inhibit cell proliferation.

In another aspect, the invention provides a method of modulating tyrosine kinase activity in a cell by administering an effective amount of a compound as set forth herein. In a further aspect, the invention provides a method of inhibiting tyrosine kinase activity in a cell by administering an effective amount of a compound as set forth herein. The present invention also provides a use of a compound as set forth herein to modulate, preferably inhibit, tyrosine kinase activity. The present invention further provides a use of a compound as set forth herein to prepare a medicament to modulate tyrosine kinase activity, preferably inhibit tyrosine kinase activity. It is appreciated that the modulation of cell proliferation by the compounds herein may be effected by other mechanisms and that tyrosine kinase modulation may be just one mechanism. Accordingly, the compounds described herein are useful in the compositions and methods set forth herein without regard to the actual mechanism contributing to their effectiveness.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE PREFERRED EMBODIMENTS

I. Definitions

The term "$C_{1-6}$alkyl" as used herein means, unless otherwise stated, straight and/or branched chain alkyl radicals containing from one to six carbon atoms and includes methyl, ethyl, propyl, isopropyl, t-butyl and the like.

The term "$C_{1-6}$alkoxy" as used herein means, unless otherwise stated, straight and/or branched chain alkoxy radicals containing from one to six carbon atoms and includes methoxy, ethoxy, propyloxy, isopropyloxy, t-butoxy and the like.

The term "$C_{1-4}$alkyl" as used herein means, unless otherwise stated, straight and/or branched chain alkyl radicals containing from one to four carbon atoms and includes methyl, ethyl, propyl, isopropyl, t-butyl and the like.

The term "$C_{1-4}$alkoxy" as used herein means, unless otherwise stated, straight and/or branched chain alkoxy radicals containing from one to four carbon atoms and includes methoxy, ethoxy, propyloxy, isopropyloxy, t-butoxy and the like.

The term "halo" as used herein means halogen and includes chloro, flouro, bromo, iodo and the like.

The term "pharmaceutically acceptable salt" means an acid addition salt which is suitable for or compatible with the treatment of patients.

The term "compound(s) as set forth herein" as used herein includes any compound of the Formulae I, II, III, and IV as defined herein (including all salts, solvates, or hydrates thereof) as well as any specific compound designated herein, such as CRIX-38, CRIX-39, CRIV-42, CRIV-46, CRVIII-33, CRVIII-34, CRVIII-35, CRVIII-50, CRVIII-51, CRVIII-52, CRVIII-53, and CRIX-79 (including all salts, solvates or hydrates thereof).

The term "pharmaceutically acceptable acid addition salt" as used herein means any non-toxic organic or inorganic salt of any base compounds represented by Formulae I-IV, or their intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluenesulfonic and methanesulfonic acids. Either the mono or di-acid salts can be formed, and such salts may exist in either a hydrated, solvated or substantially anhydrous form. In general, the acid addition salts of compounds as set forth herein are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of compounds of Formulae I-IV for laboratory use, or for subsequent conversion to a pharmaceutically acceptable acid addition salt.

The term "solvate" as used herein means a compound of Formulae I-IV, or a pharmaceutically acceptable salt of a compound of Formulae I-IV, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term an "effective amount" or a "sufficient amount" of an agent as used herein is that amount sufficient to effect beneficial or desired results, including clinical results, and, as such, an "effective amount" depends upon the context in which it is being applied and would be understood by a person skilled in the art. For example, in the context of administering an agent that modulates cell proliferation, an effective amount of an agent is, for example, an amount sufficient to achieve such a modulation in cell proliferation as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "prevention" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the frequency of, or alternatively delaying, pain sensations experienced by subjects in a treated population versus an untreated control population.

The term "modulate" as used herein includes the inhibition or suppression of a function or activity (such as cell proliferation) as well as the enhancement of a function or activity.

To "inhibit" or "suppress" or "reduce" a function or activity, such as cancer cell proliferation is to reduce the function or activity when compared to otherwise same conditions except for a condition or parameter of interest, or alternatively, as compared to another conditions.

To "enhance" or "increase" a function or activity such as cell proliferation, is to increase the function or activity when compared to otherwise same conditions except for a condition or parameter of interest, or alternatively, as compared to another conditions.

The term "animal" as used herein includes all members of the animal kingdom including human. The animal is preferably a human.

The term "a cell" as used herein includes a plurality of cells. Administering a compound to a cell includes in vivo, ex vivo and in vitro administration.

The term "abnormal cell" as used herein includes any cell type that is causitive or involved in a disease or condition and wherein it is desirable to modulate, enhance or inhibit proliferation of the abnormal cell to treat the disease or condition.

II. Compounds of the Invention

Compounds are provided which may be used to modulate cell proliferation. As such the compounds may be useful in treating cell proliferative diseases such as cancer.

Accordingly, the present invention provides compounds of Formula I, and salts, solvates or hydrates thereof:

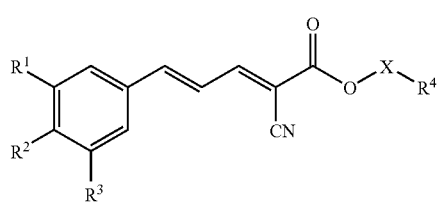

I wherein $R^1$, $R^2$ and $R^3$ are each independently selected from H, OH, $C_{1-6}$alkyl, $C_{1-6}$alkoxy, $NH_2$, $NH$—$C_{1-6}$alkyl, $N(C_{1-6}$alkyl)($C_{1-6}$alkyl), SH, S—$C_{1-6}$alkyl, $NO_2$, $CF_3$, $OCF_3$ and halo;

$R^4$ is unsubstituted Ar, or Ar substituted with 1-4 substituents, independently selected from $C_{1-6}$alkyl, $C_{1-6}$alkoxy and halo;

X is selected from $(CH_2CH_2O)_n$ and $(CH_2)_n$, and n=1-3.

In embodiments of the invention, compounds of Formula I are those in which $R^1$, $R^2$ and $R^3$ are each independently selected from H, OH, $C_{1-6}$alkyl, $C_{1-6}$alkoxy, $NH_2$, $NH$—$C_{1-6}$alkyl, $N(C_{1-6}$alkyl)($C_{1-6}$alkyl), SH, S—$C_{1-4}$alkyl, $NO_2$, $CF_3$, $OCF_3$ and halo. In preferred embodiments, $R^1$, $R^2$ and $R^3$ are each independently selected from H, OH, $C_{1-4}$alkyl, $C_{1-4}$alkoxy, $NH_2$, $NH$—$C_{1-4}$alkyl, $N(C_{1-4}$alkyl)($C_{1-4}$alkyl), $NO_2$, $CF_3$, $OCF_3$ and halo. In more preferred embodiments, $R^1$, $R^2$ and $R^3$ are each independently selected from H, OH, $OCH_3$, $NH_2$, $N(CH_3)_2$ and $NO_2$. In the most preferred embodiments, $R^1$, $R^2$ and $R^3$ are each independently selected from H, OH and $OCH_3$.

Further embodiments of the invention include compounds of Formula I wherein $R^4$ is Ar. In preferred embodiments, $R^4$ is unsubstituted Ar. Most preferably, $R^4$ is phenyl.

Further embodiments of the invention include compounds of Formula I wherein X is $(CH_2)_n$. Preferably n is 1-3; most preferably n is 1.

In a preferred embodiment of the present invention, compounds of Formula I include those in which at least one of $R^1$, $R^2$ and $R^3$ is OH, more preferably at least two of $R^1$, $R^2$ and $R^3$ are OH, while $R^4$ is Ar and n is 1-3.

The present invention also provides a compound of Formula II and salts, solvates and hydrates thereof:

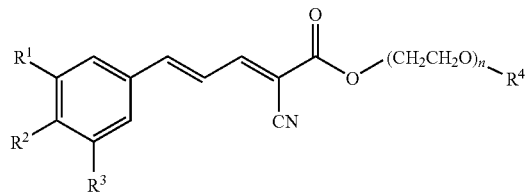

II wherein $R^1$, $R^2$, $R^3$ are each independently selected from H, OH, $C_{1-6}$alkyl, $C_{1-6}$alkoxy, $NH_2$, $NH$—$C_{1-6}$alkyl, $N(C_{1-6}$alkyl)($C_{1-6}$alkyl), SH, S—$C_{1-6}$alkyl, $NO_2$, $CF_3$, $OCF_3$ and halo;

$R^4$=$C_{1-6}$alkyl; and n=1-4.

In embodiments of the invention, compounds of Formula II are those in which $R^1$, $R^2$ and $R^3$ are each independently selected from H, OH, $C_{1-6}$alkyl, $C_{1-6}$alkoxy, $NH_2$, $NH$—$C_{1-6}$alkyl, $N(C_{1-6}$alkyl)($C_{1-6}$alkyl), SH, S—$C_{1-4}$alkyl, $NO_2$, $CF_3$, $OCF_3$ and halo. In preferred embodiments, $R^1$, $R^2$ and $R^3$ are each independently selected from H, OH, $C_{1-4}$alkyl, $C_{1-4}$alkoxy, $NH_2$, $NH$—$C_{1-4}$alkyl, $N(C_{1-4}$alkyl)($C_{1-4}$alkyl), $NO_2$, $CF_3$, $OCF_3$ and halo. In more preferred embodiments, $R^1$, $R^2$ and $R^3$ are each independently selected from H, OH, $OCH_3$, $NH_2$, $N(CH_3)_2$ and $NO_2$. In the most preferred embodiments, $R^1$, $R^2$ and $R^3$ are each independently selected from H, OH and $OCH_3$.

Further embodiments of the invention include compounds of Formula II wherein $R^4$ is $C_{1-6}$alkyl. In preferred embodiments, $R^4$ is methyl or ethyl. Most preferably, $R^4$ methyl.

Further embodiments of the invention include compounds of Formula II wherein n in 1-4. Preferably, n is 2-3; most preferably, n is 3.

In specific embodiments of the present invention, a compound of the invention is:
2-Cyano-5-(4-hydroxy-3,5-dimethoxyphenyl)-penta-2E,4E-dienoic acid benzyl ester (CRIX-38)
2-Cyano-5-(3,4-dihydroxyphenyl)-penta-2E,4E-dienoic acid benzyl ester (CRIX-39)
2-Cyano-5-(3,4-dihydroxyphenyl)-penta-2E,4E-dienoic acid 2-[2-(2-methoxyethoxy)ethoxy]ethyl ester (CRIV-42)
2-Cyano-5-(4-hydroxy-3,5-dimethoxyphenyl)-penta-2E,4E-dienoic acid 2-[2-(2-methoxyethoxy)ethoxy]ethyl ester (CRIV-46); and
2-Cyano-5-(4-hydroxy-3-methoxyphenyl)-penta-2E,4E-dienoic acid benzyl ester (CRIX-79).

Accordingly, the present invention provides compounds of Formula III, and salts, solvates or hydrates thereof:

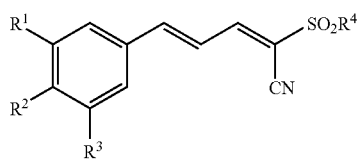

wherein
$R^1$, $R^2$ and $R^3$ are each independently selected from H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo; and
$R^4$ is selected from $C_{1-6}$alkyl, phenyl and pyridyl, wherein phenyl and pyridyl are unsubstituted or substituted with 1-4 substituents, independently selected from $C_{1-6}$alkyl, $C_{1-6}$alkoxy and halo, with the provisos that when $R^1$ and $R^3$ are both H and $R^4$ is unsubstituted phenyl, $R^2$ is not H, Cl, or $OCH_3$; when $R^1$ and $R^2$ are both H and $R^4$ is unsubstituted phenyl, $R^3$ is not $NO_2$; and when $R^1$ and $R^3$ are both H and $R^4$ is $CH_3$, $R^2$ is not $N(CH_3)_2$.

In embodiments of the invention, compounds of Formula III are those in which $R^1$, $R^2$ and $R^3$ are each independently selected from H, OH, $C_{1-6}$alkyl, $C_{1-6}$alkoxy, $NH_2$, NH—$C_{1-6}$alkyl, N($C_{1-6}$alkyl)($C_{1-6}$alkyl), SH, S—$C_{1-6}$alkyl, $NO_2$, $CF_3$, $OCF_3$ and halo. In preferred embodiments, $R^1$, $R^2$ and $R^3$ are each independently selected from H, OH, $C_{1-4}$alkyl, $C_{1-4}$alkoxy, $NH_2$, NH—$C_{1-4}$alkyl, N($C_{1-4}$alkyl)($C_{1-4}$alkyl), $NO_2$, $CF_3$, $OCF_3$ and halo. In more preferred embodiments, $R^1$, $R^2$ and $R^3$ are each independently selected from H, OH, $OCH_3$, $NH_2$, $N(CH_3)_2$ and $NO_2$. In the most preferred embodiments, $R^1$, $R^2$ and $R^3$ are each independently selected from H, OH and $OCH_3$.

Further embodiments of the invention include compounds of Formula III wherein $R^4$ is selected from $C_{1-6}$alkyl, phenyl and pyridyl, wherein phenyl and pyridyl are unsubstituted or substituted with 1-4 substituents, independently selected from $C_{1-6}$alkyl, $C_{1-6}$alkoxy and halo. In preferred embodiments of the present invention, $R^4$ is selected from $C_{1-4}$alkyl, phenyl and pyridyl, wherein phenyl and pyridyl are unsubstituted or substituted with 1-3 substituents, independently selected from $C_{1-4}$alkyl, $C_{1-4}$alkoxy and halo. In more preferred embodiments, $R^4$ is selected from $CH_3$ and phenyl, wherein phenyl is unsubstituted or substituted with 1-2 substituents, independently selected from $C_{1-4}$alkyl, $C_{1-4}$alkoxy and halo. In the most preferred embodiment $R^4$ is unsubstituted phenyl.

In a preferred embodiment of the present invention, compounds of Formula I include those in which at least one of $R^1$, $R^2$ and $R^3$ is OH, more preferably at least two of $R^1$, $R^2$ and $R^3$ are OH, while $R^4$ is selected from unsubstituted phenyl and phenyl substituted with 1-4 substituents, independently selected from $C_{1-6}$alkyl, $C_{1-6}$alkoxy and halo.

In specific embodiments of the present invention, the compounds of the invention include:
2-Benzenesulfonyl-5-(3,4-dihydroxyphenyl)-penta-2E,4E-dienenitrile (CRVIII-33)
2-Benzenesulfonyl-5-(4-hydroxy-3,5-dimethoxyphenyl)-penta-2E,4E-dienenitrile (CRVIII-34)
2-Benzenesulfonyl-5-(4-nitrophenyl)-penta-2E,4E-dienenitrile (CRVIII-35)
5-(3,4-Dihydroxyphenyl)-2-(pyridine-2-sulfonyl)-penta-2E,4E-dienenitrile (CRVIII-50)
2-(4-Chlorobenzenesulfonyl)-5-(3,4-dihydroxyphenyl)-penta-2E,4E-dienenitrile (CRVIII-51)
5-(3,4-Dihydroxyphenyl)-2-toluene4-sulfonyl)-penta-2E, 4E-dienenitrile (CRVIII-52); and
5-(3,4Dihydroxyphenyl)-2-methanesulfonyl-penta-2E,4E-dienenitrile (CRVIII-53).

The present invention includes within its scope prodrugs of the compounds of the invention. In general, such prodrugs will be functional derivatives of a compound of the invention which are readily convertible in vivo into the compound from which it is notionally derived. Conventional procedures for the selection and preparation of suitable prodrugs are described, for example, in "Design of Prodrugs" ed. H. Bundgaard, Elsevier, 1985.

The present invention includes radiolabeled forms of compounds of the invention, for example, compounds of the invention labeled by incorporation within the structure $^3H$ or $^{14}C$ or a radioactive halogen such as $^{125}I$.

III. Methods of Preparing Compounds of the Invention

In accordance with another aspect of the present invention, the compounds of the invention can be prepared by processes analogous to those established in the art. Therefore, compounds of this invention may be prepared by the reaction sequence shown in Scheme 1:

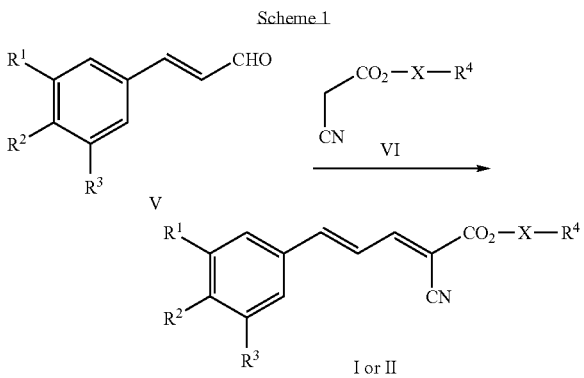

Scheme 1

Compounds of the general Formula I or II useful in the practice of this invention can be prepared by Knoevenagel condensation of α,β-unsaturated aldehydes, such as cinnamaldehyde or its various aryl-substituted homologues (V), with an α-cyano ester compound having an active α-methylene group (VI). Similar Knoevenagel condensations using ylidenemalononitriles as active α-methylene group components were described in a review (F. Freeman. Chem. Rev. 1980, V. 80, P. 329-350). Use of a reagent analogous to VI wherein the $CO_2X$ is replaced by $SO_2$ permits the preparation of compounds of Formulae III and IV. These condensations may, for example, be carried out in a polar solvent, such as ethanol, in the presence of catalytic amounts of a weak base, such as β-alanine. Reaction temperatures may be in the range of 20 to 100° C., depending on the stability of the materials used in the condensation. Depending on the reactivity of the starting reagents V and/or VI a stronger base, such as piperidine, may also be used to effect the condensation reaction.

Compounds of Formula V may be commercially available, such as cinnamaldehyde, and its 3,5-dimethoxy-4-hydroxy and 4-nitro derivatives. Other compounds of Formula V may be prepared using straightforward procedures. For example, various $R^1$, $R^2$, $R^3$-hydroxy substituted cinnamaldehydes can be prepared from the corresponding commercially available aryl substituted cinnamic acids. Scheme 2 gives an example of the preparation of 3,4-dihydroxycinnamaldehyde (caffeic aldehyde, Va) starting from 3,4-dihydroxycinnamic acid (VII).

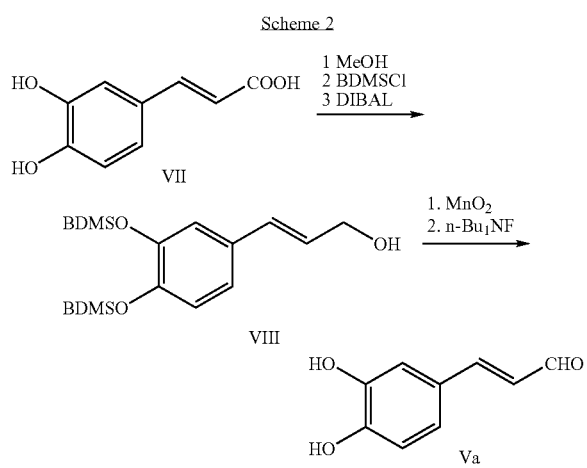

Compounds of Formula VI may be prepared, for example, by condensing cyanoacetic acid X with the appropriately substituted alcohol XI under standard conditions, as shown in Scheme 3.

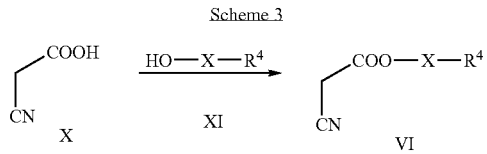

$R^1$, $R^2$, $R^3$ substituents may be also converted from one functional group to another, for example by known reduction of nitro groups into amino groups and the further transformation into dialkylamino groups, or by known conversion of hydroxy groups to halo groups.

In some cases the reactions outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of the invention may be conventional esters formed with available hydroxy, amino or carboxyl group. For example, when $R^1$, $R^2$ or $R^3$ is OH in a compound as described herein it may be acylated using an activated acid in the presence of a base, and optionally, in inert solvent (e.g., an acid chloride in pyridine). Some common esters which have been utilized as prodrugs are phenyl esters, aliphatic ($C_8$-$C_{24}$) esters, acyloxymethyl esters, carbamates and amino acid esters.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin or tributyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C.

IV. Uses

The present invention includes all uses of the compounds as set forth above, including their use in therapeutic methods and compositions for modulating cell proliferation, preferably inhibiting cell proliferation, their use in diagnostic assays, and their use as research tools.

In one aspect, the present invention provides a method for modulating cell proliferation comprising administering an effective amount of a compound of the invention to a cell or animal in need thereof. Preferably, the invention provides a method of inhibiting cell proliferation comprising administering an effective amount of a compound of the invention to a cell or animal in need thereof. In particular, the method of the invention is useful in inhibiting the proliferation of abnormal but not normal cells. As stated hereinabove, abnormal cells include any type of cell that is causative of or involved in a disease or condition and wherein it is desirable to modulate or inhibit the proliferation of the abnormal cell to treat the disease or condition.

The compounds of the invention may be very effective at killing cancer cells while at the same time not killing normal cells and therefore, may be extremely useful anti-cancer agents. Accordingly, in one embodiment, the present invention provides a method of inhibiting the proliferation of a cancer cell comprising administering an effective amount of a compound of the invention to a cell or animal in need thereof. The present invention also includes a use of a compound or composition of the invention in order to modulate, preferably inhibit, cell proliferation, preferably cancer cell proliferation. The present invention further includes a use of a compound or a composition of the invention to prepare a medicament to modulate, preferably inhibit, cell proliferation, preferably cancer cell proliferation. The cancer cell that can be treated with a compound of the invention may be any type of cancer including, but not limited to, hematopoietic malignancies, such as leukemia.

In a specific embodiment, the present invention provides a method of inhibiting the proliferation of a cell, comprising administering to a cell or animal in need thereof, an effective amount of a compound selected from:

2-Cyano-5-(4-hydroxy-3,5-dimethoxyphenyl)-penta-2E,4E-dienoic acid benzyl ester (CRIX-38);

2-Cyano-5-(3,4-dihydroxyphenyl)-penta-2E,4E-dienoic acid benzyl ester (CRIX-39);

2-cyano-5-(3,4-dihydroxyphenyl)-penta-2E,4E-dienoic acid 2-[2-(2-methoxyethoxy)ethoxy]ethyl ester (CRIV-42);

2-Cyano-5-(4-hydroxy-3,5-dimethoxyphenyl)-penta-2E,4E-dienoic acid 2-[2-(2-methoxyethoxy)ethoxy]ethyl ester (CRIV-46);

2-Cyano-5-(4-hydroxy-3-methoxyphenyl)-penta-2E,4E-dienoic acid benzyl ester (CRIX-79);

2-Benzenesulfonyl-5-(3,4-dihydroxyphenyl)-penta-2E,4E-dienenitrile (CRVIII-33)

2-Benzenesulfonyl-5-(4-hydroxy-3,5-dimethoxyphenyl)-penta-2E,4E-dienenitrile (CRVIII-34)

2-Benzenesulfonyl-5-(4-nitrophenyl)-penta-2E,4E-dienenitrile (CRVIII-35)

5-(3,4-Dihydroxyphenyl)-2-(pyridine-2-sulfonyl)-penta-2E,4E-dienenitrile (CRVIII-50)

2-(4-Chlorobenzenesulfonyl)-5-(3,4-dihydroxyphenyl)-penta-2E,4E-dienenitrile (CRVIII-51)

5-(3,4-Dihydroxyphenyl)-2-(toluene-4-sulfonyl)-penta-2E,4E-dienenitrile (CRVIII-52); and 5-(3,4-Dihydroxyphenyl)-2-methanesulfonyl-penta-2E,4E-dienenitrile (CRVIII-53).

The compounds as set forth herein may be effective as ex vivo purging agents. For ex vivo administration, cells may be removed from a patient and purged ex vivo with a compound of the invention. Such a purging should kill the abnormally proliferating cells while leaving normal cells intact. After purging, the treated cells can be washed and reintroduced into the patient.

The activity of the compounds of the invention for modulating cell proliferation can be determined using standard assays known to those skilled in the art. Examples of abnormally proliferating cells include malignant or cancerous cells as well as cells such as t-cells that over-proliferate in autoimmune disorders and graft versus host disorders, endothelial and/or epithelial cells that over-proliferate in angiogenesis, and eosinophils that over-proliferate in allergy-related conditions. To assay for efficacy in modulating cell proliferation, the cells may be cultured in the presence of one or more compounds of the invention, and the effect of the compound(s) on the proliferation of the cells can be assayed and compared to the proliferation of the cells in the absence of the compound.

The compounds of the invention may be tyrosine kinase modulators and therefore, useful in modulating tyrosine kinase activity, including the inhibition of tyrosine kinase activity, for the treatment of various conditions such as all proliferative disorders as mentioned above. Accordingly, the invention provides a method of modulating tyrosine kinase activity by administering an effective amount of a compound as set forth herein to a cell or animal in need thereof. In a further aspect, the invention provides a method of inhibiting tyrosine kinase activity by administering an effective amount of a compound as set forth herein to a cell or animal in need thereof.

While the compounds of the invention may act by modulating tyrosine kinase activity, one of skill in the art will appreciate that other modes or mechanisms of action for the compounds of the invention are possible.

The compounds as set forth herein are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds as set forth herein may be used in the form of the free base, in the form of salts, solvates and as hydrates. All forms are within the scope of the invention. Acid addition salts may be formed and provide a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of the basic compounds are preferred, all acid addition salts are useful as sources of the free base form even if the particular salt per se is desired only as an intermediate product as, for example, when the salt is formed only for the purposes of purification and identification, or when it is used as an intermediate in preparing a pharmaceutically acceptable salt by ion exchange procedures.

Pharmaceutically acceptable salts within the scope of the invention include those derived from the following acids; mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

In accordance with the methods of the invention, the described compounds or salts or solvates thereof may be administered to a patient in a variety of forms depending on the selected route of administration, as will be understood by those skilled in the art. The compositions of the invention may be administered orally or parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention or a salt or solvate thereof may be orally administered, for example, with an inert diluent or with an assimilable edible career, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally or intraperitoneally. Solutions of a compound of the invention as a free base or pharmacologically acceptable salt or solvate can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

The compounds as set forth herein may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds and/or compositions as set forth herein can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds as set forth herein may be administered initially in a suitable dosage that may be adjusted as required, depending on the clinical response.

The compounds as set forth herein may be used alone or in combination with other agents that modulate tyrosine kinase activity or in combination with other types of treatment (which may or may not modulate tyrosine kinase activity) for cell proliferative disorders. Agents known in the art that inhibit tyrosine kinase activity include, but are not limited to, antisense nucleic acid and ribozymes targeted to nucleic acid encoding a receptor tyrosine kinase, antibodies able to modulate tyrosine kinase activity and other small molecule tyrosine kinase inhibitors such as those described in U.S. Pat. Nos. 5,891,917, 5,217,999, 5,773,476, 5,935,993, 5,656,655, 5,677,329 and 5,789,427.

In addition to the above-mentioned therapeutic uses, the compounds as set forth herein are also useful in diagnostic assays, screening assays and as research tools.

In diagnostic assays the compounds as set forth herein may be useful in identifying or detecting a cell proliferative disorder. In such an embodiment, the compounds as set forth herein may be radiolabelled (as hereinbefore described) and contacted with a population of cells. The presence of the radiolabelled compound on the cells may indicate a cell proliferative disorder.

In screening assays, the compounds as set forth herein may be used to identify other compounds that modulate cell proliferation or tyrosine kinase activity. As research tools, the compounds of the invention may be used in receptor binding assays and assays to study the localization of tyrosine kinases. In such assays, the compounds may also be radiolabelled.

The following non-limiting examples are illustrative of the present invention:

EXAMPLES

Materials and Methods for Examples 1-5

$^1$H NMR spectra were obtained on a Varian Unity Plus spectrometer at 500 MHz in acetone-$d_6$ with Me4Si as an internal standard ($\delta$=0). Electrospray mass spectra were acquired on an API III+ triple quadrupole mass spectrometer (PE Sciex, Thornhill, Canada). Samples were directly introduced into the electrospray ionization source using an HPLC pump. Thin layer chromatography was performed with UV-254 aluminum-backed TLC sheets of 0.25 mm thickness (Kieselgel 60 F254, Merck, Germany). HPLC chromatograms and UV spectra were obtained on a model 600 liquid chromatograph (Waters, USA) with a model 996 PDA detector. UV spectra of the compounds were recorded from 200 to 800 nm in steps of 1.2 nm. Spectra were obtained in the mobile phase in which they were eluted from the column. The column was 5 μm Zorbax SB-CN (Agilent Technologies, USA). Gradient separations were conducted using the following buffers: (A) 0.1% $H_3PO_4$ in $H_2O$; (B) MeCN-$H_2O$, 4:1+ 0.1% $H_3PO_4$. The following gradient system was employed: 20% of the buffer B in the buffer A for 10 min, followed by linearly increasing the percentage of the buffer B from 20 to 90% during 20 min. The flow rate was 1.0 mL/min. Vacuum distillations were done using Kugelrohr apparatus (Aldrich) at stated temperatures of an oven.

4-Hydroxy-3,5-dimethoxycinnamaldehyde and 4-hydroxy-3-methoxycinnamaldehyde, as well as all other reagents were purchased from Aldrich (USA) and were used as received. Solvents were purchased from Caledon (Canada). A modified synthetic scheme [see C. M. Roifman, T. Grunberger, O. Rounova, P. Demin, and N. Sharfe. PCT Int. Appl. WO 2001079158, issued Oct. 25, 2001, 100 pp.] was used for the preparation of caffeoyl aldehyde. The direct precursor of the aldehyde, 3,4-bis-(t-butyldimethylsilyloxy)cinnamyl alcohol, was obtained as described in an article [M. Potgieter, G. L. Wenteler, and S. E. Drewes. Phytochemistry, 1988, V. 27, No. 4, P. 1101-1104].

Example 1

3,4-Dihydroxycinnamaldebyde (Caffeoyl Aldehyde)

3,4-Bis-(t-butyldimethylsilyloxy)cinnamyl alcohol (7.88 g, 20 mmol) was dissolved in 1000 mL $CH_2Cl_2$, 17.2 g activated $MnO_2$ (200 mmol) were added and the mixture was vigorously stirred for 24 h at 20° C. $MnO_2$ was filtered off and the filtrate was taken to dryness. To the obtained 3,4-bis (tBDMS)caffeoyl aldehyde 250 mL of $CHCl_3$ was added followed by addition of n-$Bu_4NF$ monohydrate (11.6 g, 40 mmol). The mixture was stirred at 20° C. for 30 min and worked up with 300 mL of 5% HCl. Chloroform layer was separated, washed with $H_2O$, dried with $Na_2SO_4$ and taken to dryness. The residue was purified on a silica gel column, eluent MeOH—$CHCl_3$, 1:4+1% AcOH. The solvents were evaporated and the crystalline residue was washed with $CHCl_3$ to give caffeoyl aldehyde (1.77 g, 54%). M.p. 200-202° C., $\lambda_{max}$ 222, 239, 249, 342 nm. $^1$H-NMR ($\delta$, ppm): 6.54 (dd, 1H, J 7.7 and 15.8 Hz, H$\alpha$), 6.91 (d, 1H, J 8.2 Hz, H5), 7.12 (br.d, 1H, J 8.2 Hz, H6), 7.21 (br.s, 1H, H2), 7.52 (d, 1H, J 15.8 Hz, H), 9.62 (d, 1H, J 7.7 Hz, CHO).

Example 2

Cyanoacetic Acid Benzyl Ester (IVa)

To a mixture of cyanoacetic acid (VII) 2.34 g (27.5 mmol) and benzyl alcohol (VIIIa) 2.70 g (25 mmol) in 60 mL of toluene 50 mg of p-TsOH was added and the mixture was refluxed in a flask with a Dean-Stark trap for 24 h. The mixture was cooled down and toluene was washed with $H_2O$ and toluene was evaporated. The residue was distilled in vacuo (Kugelrohr apparatus, 0.1 mm Hg, T. oven 170-180° C.). Yield 3.36 g (77%), a colorless oil. MS (m/z, rel. intensity, %): 167.0 ($[M+NH_4-CN]^+$, 27), 193.0 ($[M+NH_4]^+$, 100).

Example 3

Cyanoacetic Acid 2-[2-(2-Methoxyethoxy)Ethoxyl] Ester (IVb)

To a mixture of cyanoacetic acid (VII) (9.4 g, 110 mmol and 2-[2-(2-methoxyethoxy)ethoxy]ethanol (VIIIb) (16.4 g, 100 mmol) in 60 mL of toluene 50 mg of p-TsOH was added and the mixture was refluxed in a flask with a Dean-Stark trap for 24 h. The mixture was cooled down and toluene was washed with $H_2O$ and toluene was evaporated. The compound was distilled in vacuo (Kugelrohr apparatus, 0.1 mm Hg, T. oven 210° C.). Yield 19.25 g (83%), a colorless oil. MS (m/z, rel. intensity, %): 232.0 ($[M+H]^+$, 100), 249.2 ($[M+NH_4]^+$, 87).

Example 4

Knoevenagel Condensation of Substituted Acetonitriles with Hydroxyl-Substituted Cinnamaldehydes To 0.2 mmol of 3,4-dihydroxycinnamaldehyde in 3 mL EtOH a corresponding substituted acetonitrile or the like was added followed by addition of 0.4 mmol of piperidine. A dark red solution was stirred at 20° C. for 0.5 h. 0.5 mL 1 N HCl and 5 mL of $H_2O$ were added and EtOH was evaporated with the stream of $N_2$. The precipitated powder was filtered off, washed with $H_2O$ and dried in a desiccator in vacuo in the presence of solid NaOH. Yields were 55-70%. For a list of obtained products (CRIX-38, CRIX-39, CRIV-42, CRIV-46, CRIX-79, CRVIII-33, CRVIII-34, CRVIII-50, CRVIII-51, CRVIII-52, CRVIII-53) see Tables 1 and 5. For the mass spectra and UV maxima see Tables 2 and 6. For the NMR data see Tables 3 and 7.

Example 5

Knoevenagel Condensation of Substituted Acetonitriles with Nitro-Substituted Cinnamaldehydes To 0.2 mmol of 4-nitrocinnamaldehyde in 3 mL EtOH a corresponding substituted acetonitrile was added followed by addition of 0.5-1.0 mg of $\beta$-alanine. A deep yellow solution was stirred at 90° C. for 4 h. 0.5 mL 1 N HCl and 5 mL of $H_2O$ were added and EtOH was evaporated with the stream of $N_2$. The precipitated powder was filtered off, and washed with $H_2O$. The obtained yellow powder was recrystallized from EtOH-$H_2O$, the crystals were washed with $H_2O$ and dried in a desiccator in vacuo in the presence of solid NaOH. Yields were 50-60%. For the list of obtained products (CRVIII-35) see Table 5. For the mass spectra and UV maxims see Table 6. For the NMR data see Table 7.

Example 6

Effect of Test Compounds Upon Normal Bone Marrow Differentiation in Culture

A CFU-GEMM assay may be performed according to Fauser and Messner (1978, Blood, 52(6) 143-8) and Messner and Fausser (1980, Blut, 41(5) 327-33).

Example 7

Killing of Philadelphia Positive Acute Lymphoblastic Leukemia by Low-dose Test Compounds in Culture Ph+ ALL cells are plated in 1 ml volumes, in the absence of exogenous growth factors, into 35 mm petri dishes (Nunc, Gibco) containing alpha MEM (Gibco) plus 10% FCS (Cansera Rexdale, ON.) in 0.9% (vol/vol) methylcellulose (Fluka, Switzerland) with various concentrations of test compounds. Cultures are set at 37° C., 5% $CO_2$ in a humidified atmosphere. Colonies consisting of more than 20 cells are counted at 12 days or earlier using an inverted microscope.

Example 8

Killing of Philadelphia Positive Z119 Acute Lymphoblastic Leukemia Cells by Low-dose Test Compounds in Culture Z119 cells are plated in 1 ml volumes at a density of $1\times10^4$ cells/ml, in the absence of exogenous growth factors, into 35 mm petri dishes (Nunc, Gibco) containing IMDM (OCI, Toronto) plus 20% FCS (Cansera Rexdale, ON) in 0.9% (vol/vol) methylcellulose (Fluka, Switzerland) with various concentrations of test compounds. Cultures are set at 37° C., 5% $CO_2$ in a humidified atmosphere. Colonies consisting of more than 20 cells are counted at 7 days or earlier using an inverted microscope. Results see Tables 4 and 8.

Example 9

Killing of AML-3 Acute Myeloid Leukemia Cells by Low-dose Test Compounds in Culture OCI-AML-3 cells are plated in 35 mm petri dishes (Nunc, Gibco) in 1 ml volumes at a density of $3.3 \times 10^3$ cells/ml, in the absence of exogenous growth factors, containing alpha MEM plus 20% FCS (Cansera, Rexdale Ont.), and 0.9% (vol/vol) methylcellulose (Fluka, Switzerland) and various concentrations of test compounds. Cell cultures are incubated in a humidified atmosphere at 37° C. with 5% $CO_2$. Colonies containing more than 20 cells are scored, using an inverted microscope, at 5-6 days. Results see Tables 4 and 8.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Formula | Chemical name | Code |
| --- | --- | --- |
|  | 2-Cyano-5-(4-hydroxy-3,5-dimethoxyphenyl)-penta-2E,4E-dienoic acid benzyl ester | CRIX-38 |
|  | 2-Cyano-5-(3,4-dihydroxyphenyl)-penta-2E,4E-dienoic acid benzyl ester | CRIX-39 |
|  | 2-Cyano-5-(3,4-dihydroxyphenyl)-penta-2E,4E-dienoic acid 2-[2-(2-methoxyethoxy)ethoxy] ethyl ester | CRIV-42 |
|  | 2-Cyano-5-(4-hydroxy-3,5-dimethoxyphenyl)-penta-2E,4E-dienoic acid 2-[2-(2-methoxyethoxy)ethoxy] ethyl ester | CRIV-46 |
|  | 2-Cyano-5-(4-hydroxy-3-methoxyphenyl)-penta-2E,4E-dienoic acid benzyl ester | CRIX-79 |

TABLE 2

| Code | MS, m/z (rel. intensity, %) | $\lambda_{max}$, nm |
| --- | --- | --- |
| CRIX-38 | 366.0 ([M + H]$^+$, 82), 383.0 ([M + NH$_4$]$^+$, 100) | 267, 407 |
| CRIX-39 | 322.2 ([M + H]$^+$, 59), 339.0 ([M + NH$_4$]$^+$, 100) | 265, 405 |
| CRIV-42 | 378.0 ([M + H]$^+$, 28), 395.1 ([M + NH$_4$]$^+$, 100) | 266, 401 |

TABLE 2-continued

| Code | MS, m/z (rel. intensity, %) | $\lambda_{max}$, nm |
|---|---|---|
| CRIV-46 | 422.2 ([M + H]+, 71), 439.2 ([M + NH4]+, 100) | 267, 406 |
| CRIX-79 | 335.8 ([M + H]+, 100), 353.0 ([M + NH4]+, 99) | 263, 400 |

TABLE 3

| Code | H² | H³ | H⁴ | H⁵ | H⁶ | PhCH=C | PhC=CH | CH=CCN | other |
|---|---|---|---|---|---|---|---|---|---|
| CRIX-38 | 7.08 (br.s, 1H) | — | — | — | 7.08 (br.s, 1H | 7.52(d, 1H, J15.1Hz) | 7.18(dd, 1H, J11.8 and 15.1Hz) | 8.08(d, 1H, J11.8Hz) | 5.30(s, 2H, COOCH₂Ph', 7.32-7.46 (m, 5H, Ph') |
| CRIX-39 | 7.22 (d, 1H, J 2.1Hz) | — | — | 6.88 (d, 1H, J 8.1Hz) | 7.09 (dd, 1H, J 2.1 and 8.1Hz) | 7.47(d, 1H, J15.1Hz) | 7.06(dd, 1H, J11.5 and 15.1Hz) | 8.08(d, 1H, J11.5Hz) | 5.30(s, 2H, COOCH₂Ph', 7.32-7.45 (m, 5H, Ph') |
| CRIV-42 | 7.25 (br.s, 1H) | — | — | 6.90 (d, 1H, J 8.0Hz) | 7.12 (br.d, 1H, J 8.0Hz) | 7.49(d, 1H, J15.1Hz) | 7.07(dd, 1H, J11.8 and 15.1Hz) | 8.11(d, 1H, J11.8Hz) | 3.29(s, 3H, Me), 3.50; 3.60; 3.66; 3.79, 4.40(5×m, 12H, (CH₂CH₂O)₃ |
| CRIV-46 | 7.12 (br.s, 1H) | — | — | — | 7.12 (br.s, 1H) | 7.52(d, 1H, J15.3Hz) | 7.21(dd, 1H, J11.7 and 15.3Hz) | 8.06(d, 1H, J11.7Hz) | 3.28(s, 3H, Me), 3.90(s, 6H, 3- and 5-OMe), 3.47; 3.58; 3.65; 3.77; 4.38(5×m, 12H, (CH₂CH₂O)₃ |
| CRIX-79 | 7.43 (d, 1H, J 2.0Hz) | — | — | 6.92 (d, 1H, J 8.3Hz) | 7.24 (dd, 1H, J 2.0 and 8.3Hz) | 7.54(d, 1H, J15.3Hz) | 7.19(dd, 1H, J11.7 and 15.3Hz) | 8.10(d, 1H, J11.7Hz) | 3.93(s, 3H, 3-OMe), 5.32(s, 2H, COOCH₂Ph'), 7.36-7.43; 7.47 (2×m, 5H, Ph') |

TABLE 4

| Compound | ALL (Z 119) IC 50, μM | AML (OCI AML-3) IC 50, μM | NBM (BFU-E) IC 50, μM |
|---|---|---|---|
| CRIX-38 | >1.0 | >0.5 | ≦10.0 |
| CRIX-39 | ≧0.6 | =0.09 | =8.0 |
| CRIV-42 | ≧0.5 | =0.09 | ≧10.0 |
| CRIV-46 | >0.5 | ≧0.5 | ≧10.0 |

TABLE 5

| Formula | Chemical name | Code |
|---|---|---|
| | 2-Benzenesulfonyl-5-(3,4-dihydroxyphenyl)-penta-2E,4E-dienenitrile | CRVIII-33 |
| | 2-Benzenesulfonyl-5-(4-hydroxy-3,5-dimethoxyphenyl)-penta-2E,4E-dienenitrile | CRVIII-34 |
| | 2-Benzenesulfonyl-5-(4-nitrophenyl)-penta-2E,4E-dienenitrile | CRVIII-35 |
| | 5-(3,4-Dihydroxyphenyl)-2-(pyridine-2-sulfonyl)-penta-2E,4E-dienenitrile | CRVIII-50 |
| | 2-(4-Chlorobenzenesulfonyl)-5-(3,4-dihydroxyphenyl)-penta-2E,4E-dienenitrile | CRVIII-51 |
| | 5-(3,4-Dihydroxyphenyl)-2-(toluene-4-sulfonyl)-penta-2E,4E-dienenitrile | CRVIII-52 |
| | 5-(3,4-Dihydroxyphenyl)-2-methanesulfonyl-penta-2E,4E-dienenitrile | CRVIII-53 |

TABLE 6

| Code | MS, m/z (rel. intensity, %) | $\lambda_{max}$, nm |
|---|---|---|
| CRVIII-33 | 242.4 (21), 328.0 ([M + H]$^+$, 100), 345.0 ([M + NH$_4$]$^+$, 40) | 266, 406 |
| CRVIII-34 | 372.0 ([M + H]$^+$, 100), 389.0 ([M + NH$_4$]$^+$, 64) | 267, 413 |
| CRVIII-35 | 341.0 ([M + H]$^+$, 35), 358.0 ([M + NH$_4$]$^+$, 100) | 350 |
| CRVIII-50 | 329.0 ([M + H]$^+$, 100), 346.0 ([M + NH$_4$]$^+$, 12) | 265, 415 |
| CRVIII-51 | 361.8 ([M + H]$^+$, 100), 378.8 ([M + NH$_4$]$^+$, 87) | 265, 412 |
| CRVIII-52 | 341.8 ([M + H]$^+$, 19), 359.0 ([M + NH$_4$]$^+$, 100) | 265, 406 |
| CRVIII-53 | 265.8 ([M + H]$^+$, 5), 282.8 ([M + NH$_4$]$^+$, 100) | 262, 399 |

TABLE 7

| Code | H² | H³ | H⁴ | H⁵ | H⁶ | PhCH=C | PhC=CH | CH=CCN | other |
|---|---|---|---|---|---|---|---|---|---|
| CRVIII-33 | 7.22 (d, 1H, J 2.2Hz) | — | — | 6.88 (d, 1H, J 8.3Hz) | 7.11 (dd, 1H, J 2.2 and 8.3Hz) | 7.58(d, 1H, J15.0Hz) | 6.93(dd, 1H, J11.7 and 15.0Hz) | 8.10(d, 1H, J11.7Hz) | 7.70; 7.78; 7.96(3×m, 5H, Ph') |
| CRVIII-34 | 7.14 (br.s, 1H) | — | — | — | 7.14 (br.s, 1H) | 7.66(d, 1H, J15.0Hz) | 7.11(dd, 1H, J11.6 and 15.0Hz) | 8.12(d, 1H, J11.6Hz) | 7.74; 7.82; 7.99(3×m, 5H, Ph') |
| CRVIII-35 | 8.08 (m, 2H, +H6) | 8.32 (m, 2H, +H5) | — | 8.32 (m, 2H, +H3) | 8.08 (m, 2H, +H2) | 7.88(d, 1H, J15.3Hz) | 7.42(dd, 1H, J11.4 and 15.3Hz) | 8.28(d, 1H, J11.4Hz) | 7.73; 7.86; 8.04(3×m, 5H, Ph') |
| CRVIII-50 | 7.30 (d, 1H, J 2.1Hz) | — | — | 6.94 (d, 1H, J 8.3Hz) | 7.20 (dd, 1H, J 2.1 and 8.3Hz) | 7.68(d, 1H, J15.1Hz) | 7.05(dd, 1H, J11.6 and 15.1Hz) | 8.14(d, 1H, J11.6Hz) | 7.78; 8.17-8.24; 8.79 (3×m, 4H, Py) |
| CRVIII-51 | 7.28 (d, 1H, J 2.2Hz) | — | — | 6.93 (d, 1H, J 8.3Hz) | 7.18 (dd, 1H, J 2.2 and 8.3Hz) | 7.63(d, 1H, J15.1Hz) | 6.98(dd, 1H, J11.6 and 15.1Hz) | 8.14(d, 1H, J11.6Hz) | 7.76; 8.00 (2×m, 4H, Ph') |
| CRVIII-52 | 7.26 (d, 1H, J 2.1Hz) | — | — | 6.92 (d, 1H, J 8.3Hz) | 7.16 (dd, 1H, J 2.1 and 8.3Hz) | 7.60(d, 1H, J15.1Hz) | 6.96(dd, 1H, J11.6 and 15.1Hz) | 8.09(d, 1H, J11.6Hz) | 3.58(s, 3H, Ph'CH₃), 7.52; 7.86 (2×m, 4H, Ph') |
| CRVIII-53 | 7.29 (d, 1H, J 2.2Hz) | — | — | 6.93 (d, 1H, J 8.2Hz) | 7.17 (dd, 1H, J 2.2 and 8.3Hz) | 7.57(d, 1H, J15.0Hz) | 7.01(dd, 1H, J11.5 and 15.0Hz) | 7.94(d, 1H, J11.5Hz) | 3.23(s, 3H, SO₂Me) |

TABLE 8

| Compound | ALL (Z 119) IC 50, μM | AML (OCI AML-3) IC 50, μM | NBM (BFU-E) IC 50, μM |
|---|---|---|---|
| CRVIII-33 | ≧0.55 | >0.5 | =12.0 |
| CRVIII-34 | >1.0 | >0.5 | ≦10.0 |
| CRVIII-35 | >1.0 | >0.5 | >5.0 |
| CRVIII-50 | ≧0.17 | ≧0.25 | ≦5.0 |
| CRVIII-51 | =0.23 | 0.25-0.5 | ≧5.0 |
| CRVIII-52 | 0.25-0.5 | 0.25-0.5 | ≦10.0 |
| CRVIII-53 | 0.45 | 0.25-0.5 | ≦10.0 |

What is claimed is:

1. A compound of Formula I, or a salt thereof:

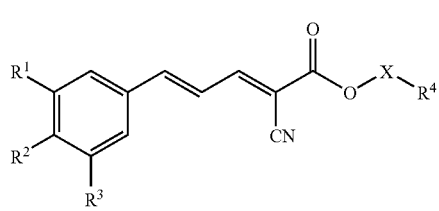

I wherein
$R^1$, $R^2$ and $R^3$ are each independently selected from H, OH, $C_{1-6}$alkyl, $C_{1-6}$alkoxy, $NH_2$, $NH-C_{1-6}$alkyl, $N(C_{1-6}$alkyl$)(C_{1-6}$alkyl$)$, SH, $S-C_{1-6}$alkyl, $NO_2$, $CF_3$, $OCF_3$ and halo;

$R^4$ is unsubstituted Ar, or Ar substituted with 1-4 substituents, independently selected from $C_{1-6}$alkyl, $C_{1-6}$alkoxy and halo;

X is selected from $(CH_2CH_2O)_n$ and $(CH_2)_n$, and n=1-4.

2. The compound according to claim 1, wherein $R^1$, $R^2$ and $R^3$ and are each independently selected from H, OH, $C_{1-4}$alkyl, $C_{1-4}$alkoxy, $NH_2$, $NH-C_{1-4}$alkyl, $N(C_{1-4}$ alkyl$)(C_{1-4}$alkyl$)$, $NO_2$, $CF_3$, $OCF_3$ and halo;

$R^4$ is $C_{1-6}$alkyl,

X is $(CH_2CH_2O)_n$, and n=1-4.

3. The compound according to claim 1, wherein $R^1$, $R^2$ and $R^3$ are each independently selected from H, OH, $C_{1-4}$alkyl, $C_{1-4}$alkoxy, $NH_2$, $NH-C_{1-4}$alkyl, $N(C_{1-4}$alkyl$)(C_{1-4}$alkyl$)$, $NO_2$, $CF_3$, $OCF_3$ and halo.

4. The compound according to claim 3, wherein $R^1$, $R^2$ and $R^3$ are each independently selected from H, OH, $OCH_3$, $NH_2$, $N(CH_3)_2$ and $NO_2$.

5. The compound according to claim 4, wherein $R^1$, $R^2$ and $R^3$ are each independently selected from H, OH, and $OCH_3$.

6. The compound according to claim 1, wherein $R^4$ is unsubstituted Ar.

7. The compound according to claim 6, wherein $R^4$ is phenyl.

8. The compound according to claim 2, wherein $R^4$ is methyl or ethyl.

9. The compound according to claim 8, wherein $R^4$ is methyl.

10. The compound according to claim 9, wherein n is 2-3.

11. The compound according to claim 10, wherein n is 3.

12. A compound selected from:

2-Cyano-5-(4-hydroxy-3,5-dimethoxyphenyl)-penta2E, 4E-dienoic acid benzyl ester (CRIX-38)

2-Cyano-5-(3,4-dihydroxyphenyl)-penta-2E,4E-dienoic acid benzyl ester (CRIX-39)

2-Cyano-5-(3,4-dihydroxyphenyl)-penta-2E,4E-dienoic acid 2-[2-(2-methoxyethoxy)ethoxy]ethyl ester (CRIV-42)

2-Cyano-5-(4-hydroxy-3,5-dimethoxyphenyl)-penta-2E, 4E-dienoic acid 2-[2-methoxyethoxy)ethoxy]ethyl ester (CRIV46); and 2-Cyano-5-(4-hydroxy-3-methoxyphenyl)-penta-2E,4E-dienoic acid benzyl ester (CRIX-79).

13. A composition comprising a compound according to any one of claims 1 to 12 in admixture with a pharmaceutically acceptable diluent or carrier.

14. The compound according to claim 1 in substantially anhydrous form.

15. The compound according to claim 1 in crystalline form.

* * * * *